United States Patent [19]

Colaianne et al.

[11] Patent Number: 4,603,225

[45] Date of Patent: Jul. 29, 1986

[54] PROCESS FOR SEPARATING DIMETHYL ETHER FROM A HYDROCARBON MIXTURE CONTAINING THE SAME

[75] Inventors: James Colaianne; Thomas J. Junker; Lawrence Saroff, all of Pittsburgh, Pa.

[73] Assignee: Dravo Corporation, Pittsburgh, Pa.

[21] Appl. No.: 774,924

[22] Filed: Sep. 11, 1985

[51] Int. Cl.$^4$ .................. C07C 41/05; C07C 41/34; C07C 7/10

[52] U.S. Cl. .................................. 568/697; 568/699; 585/331; 585/864

[58] Field of Search ............... 568/697, 699; 585/864, 585/331

[56] References Cited

U.S. PATENT DOCUMENTS

| | | |
|---|---|---|
| 3,847,756 | 11/1974 | Statman et al. . |
| 4,118,425 | 10/1978 | Herbstman . |
| 4,144,138 | 3/1979 | Rao et al. . |
| 4,218,569 | 8/1980 | Chase et al. . |
| 4,302,298 | 11/1981 | Mikitenko et al. . |
| 4,307,254 | 12/1981 | Smith et al. ......................... 568/697 |
| 4,334,964 | 6/1982 | Prezelj et al. . |
| 4,465,870 | 8/1984 | Herskovits . |
| 4,479,018 | 10/1984 | Van Pool . |
| 4,546,206 | 12/1985 | Neier et al. ......................... 568/697 |

*Primary Examiner*—Howard T. Mars
*Attorney, Agent, or Firm*—Parmelee, Miller, Welsh & Kratz

[57] ABSTRACT

A process for separating dimethyl ether from a hydrocarbon mixture which comprises contacting the hydrocarbon mixture with an aqueous solution containing a polar oxygenated hydrocarbon having a polarity of about 1.4 to about 2.0 Debyes.

27 Claims, 1 Drawing Figure

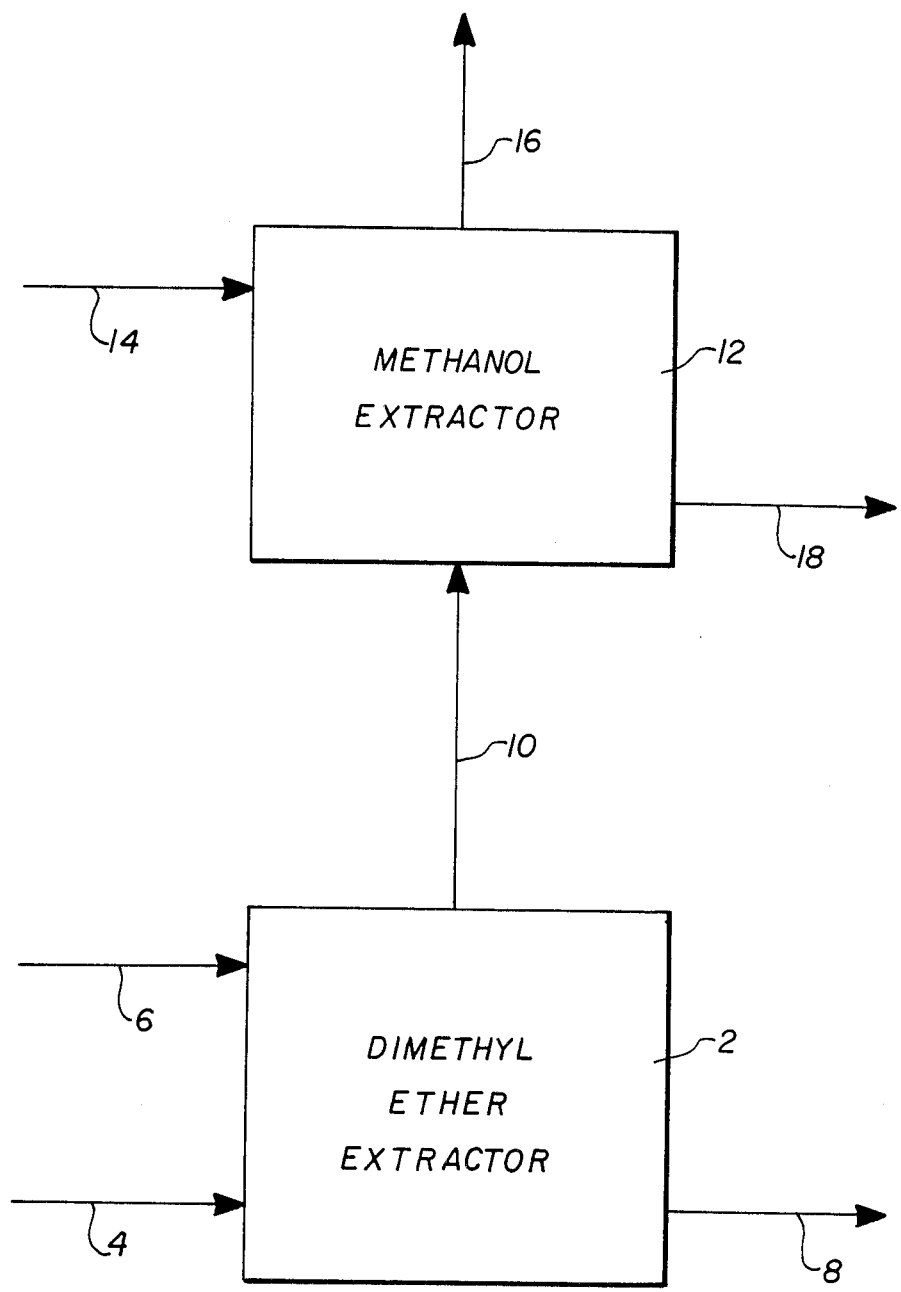

ns, for example, a hydrocarbon mixture contain-

PROCESS FOR SEPARATING DIMETHYL ETHER FROM A HYDROCARBON MIXTURE CONTAINING THE SAME

FIELD OF THE INVENTION

This invention relates to a process for separating dimethyl ether from a hydrocarbon mixture containing the same which comprises contacting said hydrocarbon mixture with an aqueous solution containing a polar oxygenated hydrocarbon having a polarity of about 1.4 to about 2.0 Debyes.

BACKGROUND OF THE INVENTION

The removal of dimethyl ether from a hydrocarbon mixture is difficult and costly. Distillation will result in the unacceptable loss of desired hydrocarbons, requiring high energy usage, in the volatility range of the dimethyl ether, while extraction with water is inefficient and costly because of the copious amounts of water needed and the large number of equilibrium stages required. The removal of dimethyl ether from a hydrocarbon mixture can be a serious problem commercially. For example, a refinery stream containing hydrocarbons having from 3 to 6 carbon atoms, including isobutylene, can be treated with methanol in the presence of an acid catalyst to cause a reaction between the olefin and the alcohol to form an alkyl ether, such as methyl tertiary butyl ether (MTBE). This can be carried out, for example, in a catalytic distillation column, wherein the feed is introduced as a side stream into the column containing the acid catalyst, a substantially pure product MTBE is continuously removed from the base of the column and a raffinate stream containing the remainder of the contents thereof, including dimethyl ether, is removed overhead. MTBE is used as an environmentally acceptable high octane enhancer for motor gasoline.

The overhead stream defined above contains hydrocarbons, including unreacted olefins, some unreacted methanol, water and dimethyl ether, formed from the dehydration of methanol, and can be charged to an alkylation plant wherein olefins can be reacted with an isoparaffin, such as isobutane, in the presence of an alkylation catalyst to form additional high octane gasoline components. However, when the alkylation catalyst is hydrogen fluoride, the presence of methanol, water and dimethyl ether in the feed to the alkylation reactor is highly detrimental, since they adversely affect the catalytic activity of the hydrogen fluoride catalyst, increasing acid loss and significantly lowering the octane value of the alkylate. The removal of water and methanol from the alkylation feed is not difficult. For example, the alkylation feed can be passed through dryers to remove water therefrom. Methanol can be removed from the alkylation stream by known processes, for example, by extraction with water. However, the removal of dimethyl ether from the alkylation stream cannot be done economically by use of distillation or a simple water wash.

Many references exist showing the removal of undesired components from a hydrocarbon stream. Thus, Brown et al in U.S. Pat. No. 3,846,088 disclose a process wherein an alcohol is reacted with a hydrocarbon stream containing a tertiary olefin to produce an ether; unreacted hydrocarbons are removed from the reaction product and the bottoms containing unreacted alcohol are washed with water to reduce the alcohol content thereof. U.S. Pat. No. 3,847,756 to Statman et al discloses a process for the purification of a stream containing diethyl ether which comprises feeding the same to a distillation column, introducing water at a higher level in the column and removing pure diethyl ether from the column just below the top of the column, while low-boiling impurities are removed from the top of the column and high-boiling impurities are removed from the bottom of the column. In U.S. Pat. No. 4,118,425 to Herbstman there is disclosed a process wherein a crude mixture containing ethers, such as the methyl ether of tertiary butanol, prepared by reacting methanol and isobutene in the presence of hydrocarbons, is subjected to extraction to remove unreacted excess methanol therefrom using water. Rao et al in U.S. Pat. No. 4,144,138 disclose a process wherein methyl tertiary butyl ether is recovered by azeotropic distillation to obtain a methanol-ether overhead azeotrope which is then water washed. The water washing results in a pure ether raffinate and an ether-methanol bottom product. The bottoms are then azeotropically distilled to give an ether-methanol overhead that is recycled to the water washing step. Chase et al in U.S. Pat. No. 4,218,569 relate to a process wherein an etherification crude product containing residual methanol is fractionally distilled to obtain a distillate containing methanol and hydrocarbons and the distillate is then contacted with a glycol to remove the methanol therefrom. The process defined in U.S. Pat. No. 4,302,298 to Mikitenko et al isolates methyl tertiary butyl ether in the reaction product of methanol with a $C_4$-hydrocarbon cut containing isobutene comprising fractionation to separate methyl tertiary butyl ether therefrom, the remainder of the reaction product containing $C_4$-hydrocarbons and methanol is water washed, a portion of the separated $C_4$-hydrocarbons from the water wash is recycled to the distillation zone and the water-methanol phase from the washing is distilled to separate the methanol therefrom. Prezelj et al in U.S. Pat. No. 4,334,964 relate to a process wherein an etherification stream is water washed to extract alcohol components therefrom, the extractant is distilled to recover methanol and a tertiary alcohol side stream is removed from the distillation zone. Herskovits in U.S. Pat. No. 4,465,870 states that he can use a solid regenerable sorbent to remove undesirable compounds such as water, methanol or ether, from a hydrocarbon recycle stream withdrawn from an etherification process. In U.S. Pat. No. 4,479,018 to Van Pool there is disclosed a process wherein a mixture of olefins containing isobutylene is reacted with methanol to form a product ether, the ether is removed from the total product and the remainder of the product containing unreacted olefins and unreacted methanol is washed with water to remove methanol therefrom.

None of the above references, alone or in combination, discloses or teaches the novel process herein, namely, the removal of dimethyl ether from a hydrocarbon mixture containing the same by contacting said hydrocarbon mixture with an aqueous solution containing a polar oxygenated hydrocarbon having a polarity of about 1.4 to about 2.0 Debyes specifically as defined herein.

SUMMARY OF THE INVENTION

This invention relates to a process for removing dimethyl ether from a hydrocarbon mixture containing the same, for example, a hydrocarbon mixture containing olefins and small amounts of methanol and dimethyl ether, that is to be contacted with an isoparaffin in the presence of an alkylation catalyst to obtain an alkylation product predominating in isooctane, which comprises contacting said hydrocarbon mixture with an aqueous solution containing a polar oxygenated hydrocarbon having a polarity of about 1.4 to about 2.0 Debyes, such as methanol.

BRIEF DESCRIPTION OF THE DRAWING

The attached drawing is a schematic illustration of an embodiment of the present invention.

DETAILED DESCRIPTION OF THE PROCESS

In accordance with the novel process defined and claimed herein dimethyl ether is separated from a hydrocarbon mixture containing the same by contacting said hydrocarbon mixture with an aqueous solution containing a polar oxygenated hydrocarbon having a polarity of about 1.4 to about 2.0 Debyes.

Any aliphatic hydrocarbon mixture containing dimethyl ether can be treated in accordance with the process defined and claimed herein to separate dimethyl ether therefrom. In general, however, the hydrocarbon mixture can contain saturated and/or unsaturated hydrocarbons having from 3 to 6 carbon atoms, more particularly 3 to 5 carbon atoms. In most cases, the hydrocarbon mixture will predominate in $C_4$-hydrocarbons. Specific examples of hydrocarbons that can be present include saturated hydrocarbons, such as propane, n-butane, i-butane, n-pentane, 2-methyl butane, hexane, etc., and unsaturated hydrocarbons, such as propene, 1-butene, trans/cis 2-butene, 1-pentene, 2-methyl butene, 2-hexene, etc. Included among the commercial hydrocarbon streams that can be treated herein are those containing the residual product resulting from the reaction of a refinery hydrocarbon stream containing at least one olefinic component, for example, isobutylene, with methanol, in the presence of an acid catalyst to form an ether, such as methyl tertiary butyl ether (MTBE). As noted above, after removal of MTBE from the reaction mixture, the reaction product can contain unreacted olefins and other hydrocarbons, unreacted methanol, which can be easily separated therefrom, and small amounts of dimethyl ether, which cannot be easily and economically removed therefrom. In a preferred embodiment, a hydrocarbon reaction product, as defined above, is treated herein to remove methanol and dimethyl ether therefrom.

The amount of dimethyl ether that will be in the hydrocarbon mixture defined above can vary over a wide range; that is, from about 10 to about 2000 parts per million by weight (ppm) but generally in the range of about 200 to about 600 ppm, based on the weight of the hydrocarbons in the mixture.

The hydrocarbon mixture defined above containing dimethyl ether is treated with an aqueous solution of a polar oxygenated hydrocarbon, generally having a greater solubility in water than in the defined hydrocarbons, for the purpose of removing dimethyl ether therefrom. The polar oxygenated hydrocarbon will have a polarity of about 1.4 to about 2.0 Debyes, preferably in the range of about 1.4 to about 1.7 Debyes. A Debye is a measurement of a dipole moment of a molecule. See the Encyclopedia of Chemistry; pages 767 to 769 G. L. Clark, Editor, Reinhold Publishing Corporation, New York, 1957. Examples of polar oxygenated hydrocarbons that can be used include alcohols having from 1 to 3 carbon atoms, preferably from 1 to 2 carbon atoms, such as methanol, ethanol, n-propanol and isopropanol.

The amount of polar oxygenated hydrocarbon compound that is in the aqueous solution used to treat the hydrocarbon mixture defined above can vary over a wide range, but generally will be within the range of about 0.5 to about 40 weight percent, preferably about 2 to about 10 weight percent, based on the total weight of the aqueous solution.

The amount of aqueous solution containing the polar oxygenated compound used to treat the hydrocarbon mixture containing dimethyl ether can also be varied over a wide range, but in general can be in a weight ratio of aqueous solution to hydrocarbon mixture of about 1:1 to about 5:1, preferably in the weight ratio range of about 1.5:1 to about 3:1.

The means required to remove dimethyl ether from the hydrocarbon mixture are not critical as long as effective contact is maintained between the hydrocarbon mixture and the aqueous solution containing the polar oxygenated compound. The temperature of treatment can be, for example, in the range of about 35° to about 180° F., but generally temperatures of about 70° to about 100° F. are preferred. Any pressure sufficient to maintain the hydrocarbons in the mixture substantially in the liquid phase can be used. Thus, the pressure can be in the range of about 65 to about 300 psia (pounds per square inch absolute), or even higher, but generally pressures of about 100 to about 200 psia are sufficient. Since the extraction procedure defined herein is an equilibrium-staged process, it can be carried out using from 1 to 30 theoretical equilibrium stages, preferably from 3 to 10 theoretical equilibrium stages. By a "theoretical equilibrium stage", we mean a stage in a process wherein no further change in concentration would occur within such stage after a longer contact time.

Contact between the hydrocarbon mixture being treated and the aqueous solution containing the polar oxygenated hydrocarbons can be effected in any desired manner. Thus, the hydrocarbon mixture and the aqueous solution can be brought together, under the conditions defined above, mixed until the dimethyl ether portions itself in the aqueous phase, and then the hydrocarbon phase and aqueous phase are separated from each other following any suitable procedure, for example, decantation. In a preferred embodiment, the desired extraction is carried out by flowing a stream of the hydrocarbon mixture and a stream of the aqueous solution countercurrently to each other, whereby the aqueous solution extracts the dimethyl ether from the hydrocarbon mixture.

The hydrocarbon mixture containing dimethyl ether, after treatment with the aqueous solution containing the defined polar oxygenated hydrocarbon, will have had its dimethyl ether content reduced to a level wherein it contains from about 0 to about 25 ppm, generally within the range of about 5 to about 10 ppm, of dimethyl ether.

In the preferred embodiment herein the hydrocarbon mixture treated is one containing hydrocarbons having from 3 to 6 carbon atoms, including isobutylene, which has been treated with methanol to obtain a reaction product containing unreacted hydrocarbons, methyl tertiary butyl ether, unreacted methanol and dimethyl ether and from which methyl tertiary butyl ether has been separated therefrom. After removal of dimethyl ether from the latter hydrocarbon product, as defined above, the remainder of said latter hydrocarbon product is subjected to an equilibrium-staged extraction with water, in any conventional manner, to remove methanol therefrom. Preferably, such extraction is carried out by flowing water countercurrently to the hydrocarbon stream. The amount of water needed is not critical and can be varied over a wide range. In general, the amount used is dependent upon several primary factors, the quantity of hydrocarbon, methanol present in the stream to be treated and the temperature of the streams. The hydrocarbon mixture after treatment will be substantially free of dimethyl ether and methanol and can then be used in an alkylation reactor using hydrogen fluoride catalyst.

DESCRIPTION OF PREFERRED EMBODIMENT

The novel process herein can better be illustrated by the following in reference to FIG. 1 of the drawing. A hydrocarbon feedstock containing isobutylene was treated with methanol in the presence of an acid catalyst to obtain a hydrocarbon mixture containing methyl tertiary butyl ether. Methyl tertiary butyl ether was removed from the latter hydrocarbon mixture, and the remainder was the feedstock used herein.

Referring to the drawing, the latter feedstock was introduced into the base of dimethyl ether extractor 2 by line 4 and was passed upwardly therethrough. An aqueous methanol solution was introduced into dimethyl ether extractor 2 adjacent the top thereof by line 6 and passed downwardly therethrough. The extract, containing substantially all of the dimethyl ether that was in line 4, was removed from the base of dimethyl ether extractor 2 by line 8.

The raffinate from the dimethyl ether extractor 2 was removed from the top thereof by line 10 and passed upwardly through methanol extractor 12. Water was introduced into methanol extractor 12 by line 14 and passed downwardly therethrough countercurrently to the raffinate from dimethyl ether extractor 2. A raffinate, substantially free of dimethyl ether and methanol, was removed overhead from methanol extractor 12 by line 16 and the extract phase by line 18 at the base thereof. The results obtained are summarized in the following Table I.

product can be passed to a hydrofluoric acid catalyzed alkylation process, since no appreciable amount of dimethyl ether or methanol is present therein. The extract in line 18 can be discarded and/or can be added to the feedwater in line 6 to reduce water requirement in dimethyl ether extractor 2. The extract in line 8 can be further processed to remove dimethyl ether therefrom using conventional means, such as by flashing or distillation.

Obviously, many modifications and variations of the invention, as hereinabove set forth, can be made without departing from the spirit and scope thereof, and therefore only such limitations should be imposed as are indicated in the appended claims.

We claim:

1. A process for separating dimethyl ether from a hydrocarbon mixture containing the same which comprises contacting said hydrocarbon mixture with an aqueous solution containing a polar oxygenated hydrocarbon having a polarity of about 1.4 to about 2.0 Debyes.

2. The process of claim 1 wherein said polar oxygenated hydrocarbon has a polarity of about 1.4 to about 1.7 Debyes.

3. The process of claim 1 wherein said polar oxygenated hydrocarbon is selected from the group consisting of alcohols having 1 to 3 carbon atoms.

4. The process of claim 3 wherein said polar oxygenated hydrocarbon is an alcohol having from 1 to 2 carbon atoms.

5. The process of claim 4 wherein said polar oxygenated hydrocarbon is methanol.

6. The process of claim 4 wherein said hydrocarbon mixture contains from about 10 to 2000 ppm of dimethyl ether.

7. The process of claim 6 wherein said hydrocarbon mixture contains from about 200 to about 600 ppm dimethyl ether.

8. The process of claim 1 wherein said hydrocarbon mixture contains hydrocarbons having from 3 to 6 carbon atoms.

9. The process of claim 8 wherein said hydrocarbon mixture contains hydrocarbons having from 3 to 5 carbon atoms.

10. The process of claim 8 wherein said hydrocarbon mixture is composed of a stream containing at least one olefin, methanol and dimethyl ether.

11. The process of claim 10 wherein said olefin is isobutylene.

12. The process of claim 1 wherein said aqueous solution contains from about 0.5 to about 40 weight percent of said polar oxygenated hydrocarbon.

TABLE I

| Component | Amount of Component in Pounds Per Hour in Each of Lines | | | | | | |
|---|---|---|---|---|---|---|---|
| | 4 | 6 | 8 | 10 | 14 | 16 | 18 |
| Propane | 326 | 0 | 25 | 301 | 0 | 300.5 | 0.5 |
| Iso Butane | 14,185 | 0 | 335 | 13,850 | 0 | 13,817 | 33 |
| Iso Butene | 421 | 0 | 9 | 412 | 0 | 412 | 0 |
| Normal Butane | 3,440 | 0 | 81 | 3,359 | 0 | 3,348 | 11 |
| Trans-2-Butene | 8,853 | 0 | 184 | 8,669 | 0 | 8,651 | 18 |
| Cis-2-Butene | 4,452 | 0 | 93 | 4,359 | 0 | 4,350 | 9 |
| Water | 7 | 85,500 | 85,481 | 26 | 3,000 | 24 | 3,001 |
| Methanol | 15 | 4,500 | 4,467 | 48 | 0 | 0.03 | 47.97 |
| Dimethyl Ether | 9 | 0 | 8.95 | 0.05 | 0 | 0.05 | 0.05 |
| Temperature, °F. | 125 | 95 | 99 | 95 | 80 | 94 | 88 |
| Pressure, PSIA | 145 | 145 | 145 | 145 | 145 | 145 | 145 |

The data in Table 1 clearly illustrate the effectiveness of the novel process defined and claimed herein. The feedstock carried 9 pounds per hour of dimethyl ether, of which 8.95 pounds per hour were removed by the extract phase in line 8, a reduction of better than 99 percent. Although some methanol was present in feedline 4 and methanol was used in dimethyl extractor 2 to remove dimethyl ether from the feedstock, note that the raffinate phase in line 16 was substantially devoid of methanol. Consequently, the raffinate phase in line 16 can be dewatered, using any standard dewatering procedure, typical to an alkylation plant, and the remaining 13. The process of claim 12 wherein said aqueous solution contains from about 2 to about 10 weight percent of said polar oxygenated hydrocarbon.

14. The process of claim 1 wherein the weight ratio of said aqueous solution to said hydrocarbon mixture is in the range of about 1:1 to about 5:1.

15. The process of claim 14 wherein the weight ratio of said aqueous solution to said hydrocarbon mixture is in the range of about 1.5:1 to about 3:1.

16. The process of claim 1 wherein said contact is carried out of a temperature of about 35° to about 180° F. and a pressure higher than about 65 psia.

17. The process of claim 16 wherein said contact is carried out at a temperature of about 70° to about 100° F. and a pressure of about 100 to about 200 psia.

18. The process of claim 1 wherein said hydrocarbon mixture contains hydrocarbons having from 3 to 6 carbon atoms and from about 10 to about 2000 ppm of dimethyl ether, said aqueous solution contains from about 0.5 to about 40 weight percent of said polar oxygenated hydrocarbon and weight ratio of said aqueous solution to said hydrocarbon mixture is in the range of about 1:1 to about 5:1.

19. The process of claim 18 wherein said hydrocarbon mixture contains hydrocarbons having from 3 to 5 carbon atoms and from about 200 to about 600 ppm of dimethyl ether, said polar oxygenated compound has a polarity of about 1.4 to about 1.7 Debyes, said aqueous solution contains from about 2 to about 10 weight percent of said polar oxygenated hydrocarbon and the weight ration of said aqueous solution to said hydrocarbon mixture is in the range of about 1.5:1 to about 3:1.

20. The process of claim 18 wherein said polar oxygenated compound is an alcohol.

21. The process of claim 19 wherein said polar oxygenated compound is an alcohol.

22. The process of claim 20 wherein said alcohol is methanol.

23. The process of claim 21 wherein said alcohol is methanol.

24. In a process wherein a hydrocarbon stream containing from 3 to 6 carbon atoms, including isobutylene, is treated with methanol, to obtain a product mixture containing unreacted hydrocarbons, methyl tertiary butyl ether, unreacted methanol, and dimethyl ether, and wherein methyl tertiary butyl ether is separated from said product mixture, the improvement which comprises contacting the remainder of said product mixture, after said separation, with an aqueous solution containing a polar oxygenated hydrocarbon having a polarity of about 1.4 to about 2.0 Debyes to remove dimethyl ether therefrom and thereafter subjecting the remaining product to extraction with water to remove methanol therefrom.

25. The process of claim 24 wherein said polar oxygenated hydrocarbon has a polarity of about 1.4 to about 1.7 Debyes.

26. The process of claim 25 wherein said polar oxygenated hydrocarbon is methanol.

27. The process of claim 24 wherein the remainder of said product after removal of methanol therefrom is passed to a hydrofluoric acid alkylation unit.

* * * * *